United States Patent [19]

Cloutier

[11] 4,220,146
[45] Sep. 2, 1980

[54] BIPLANAR JOINT DISTRACTOR

[76] Inventor: Jean-Marie Cloutier, 12 Aberdeen, Westmount, Quebec, Canada, H3Y 3A4

[21] Appl. No.: 4,557

[22] Filed: Jan. 18, 1979

[51] Int. Cl.³ .................... A61F 5/00; A61B 17/18
[52] U.S. Cl. .................... 128/69; 128/84 B; 128/92 A; 128/92 E; 128/303 R
[58] Field of Search ............. 128/92 A, 92 R, 92 E, 128/303 R, 84 B, 84 C, 84 R, 75, 69

[56] References Cited
U.S. PATENT DOCUMENTS

| | | | |
|---|---|---|---|
| 2,055,024 | 9/1936 | Bittner, Jr. | 128/84 B |
| 3,976,061 | 8/1976 | Volkov et al. | 128/92 A |

Primary Examiner—Ronald L. Frinks

[57] ABSTRACT

A biplanar joint distractor to be used in arthroplasty for reversibly separating two articulated bones joined by at least one ligament while preserving the latter. The joint distractor comprises a pair of pins each to be removably introduced transversally through one of the bones to be separated and a pair of mechanically adjustable means fixable onto the pins at a predetermined distance on both sides of the bones for forcing the latter apart. The adjustable means comprises a pair of at least partially threaded rods extending generally perpendicular to said pins; first means for rigidly fixing each rod by one of its ends to one end of said pins; second means slidably mounted on each of said rods, including means thereon for clamping the ends of the other pin; and a pair of operating wheels each threadably mounted on the threaded portion of one of said rods between said first and second means. In operation, rotation of the operating wheels in one direction brings the same in contact against the second means and forces the latter to slide along the rods apart from the first means while rotation of the wheels in the other direction lets the second means freely slide back along the rods towards the first means.

2 Claims, 3 Drawing Figures

BIPLANAR JOINT DISTRACTOR

The present invention relates to a biplanar joint distractor especially designed for reversibly separating two articulated bones joined and stabilized a ligamentous structure while preserving latter, to allow for restoration of joint stability in joint arthroplasty.

As is known, the stability of the natural joints, such as, for example, knees and elbows, essentially depends on the ligamentous structures of the articular surfaces.

For example, the stability of the knee depends on the collateral and cruciate ligaments which are responsible for the transverse and anter-posterior stability of the knee, respectively. These ligaments are made up of bands of fibers which tight up or loosen by alteration of their overall length as the knee flexes.

It is therefore readily apparent that preservation of the ligamentous structure in joint arthroplasty and more especially in total joint arthroplasty, is critical to allow for complete restoration of the stability of the joint, more especially in flexion and extension.

It is an object of the present invention to provide a joint distractor which allows the surgeon to preserve the ligaments of the joint in joint arthroplasty and to reestablish at will the lengths of the same after the operation so as to restore the natural joint stability.

It is another object of the invention to provide a joint distractor which allows the surgeon to obtain more working space in the joint and to immobilize the latter throughout the procedure.

It is a further object of the invention to provide a joint distractor which allows for distraction of the joint in either full extension or at 90 degrees flexion without having to be dismantled, and individual, accurate reliable adjustment of the axial alignments of the limbs of the bones.

These objects are achieved with a biplanar joint distractor comprising a pair of pins each to be removably introduced transversally through one of the bones to be separated and a pair of mechanically adjustable means fixable onto the pins at a predetermined distance on both sides of the bones for forcing the same apart.

In accordance with the present invention, the adjustable means comprise:
- a pair of at least partially threaded rods extending generally perpendicular to the pins;
- first means for rigidly fixing each rod by one of its ends to one end of one of the pins;
- second means slidably mounted on each of the rods, including means thereon for clamping the ends of the other pin; and
- a pair of operating wheels each threadably mounted on the threaded portion of one of the rods between the first and second means.

The rotation of the operating wheels in one direction brings the same in contact against the second means and forces the latter to slide along the rods apart from the first means while rotation of the wheels in the other direction lets the second means freely slide back along the rods towards the first means.

Preferably, the first means comprises a U-shaped member with two parallel arms defining a slot in which is inserted the upper end of one of the rods and a first, partially threaded fixing pin passing through and extending outwards the surfaces of both of the arms in a direction perpendicular to the axis of the slot. This first fixing pin comprises a first, external, not threaded portion with a transversal hole in which is inserted the end of one of the pin, and a second, external, threaded portion. The first means also comprises a first serrated wheel threaded onto the second portion of the first fixing pin. In operation, rotation of the first serrated wheel downwards onto the first fixing pin allows for simultaneous clamping of the one pin by contact against the surface of one of the arms and of the one rod by contraction of the arms.

Also preferably, the second means comprises a L-shaped member having a vertical, longer arm with a cylindrical hole extending along its longitudinal axis, in which is slidably inserted the lower end of one of the rods, and a horizontal shorter arm with another cylindrical hole perpendicular to the first one and in which is inserted a second fixing pin having a first, external, not threaded portion with a transversal hole in which is inserted the end of the other pin and a second external, threaded portion. The second means also comprises a second serrated wheel threaded onto the second portion of the second fixing pin. In operation, rotation of the second serrated downwards onto the second fixing pin allows for clamping of the other pin by contact against the surface of the horizontal, shorter arm.

The invention will be better understood with reference to the accompanying drawings, wherein.

Figure 1:
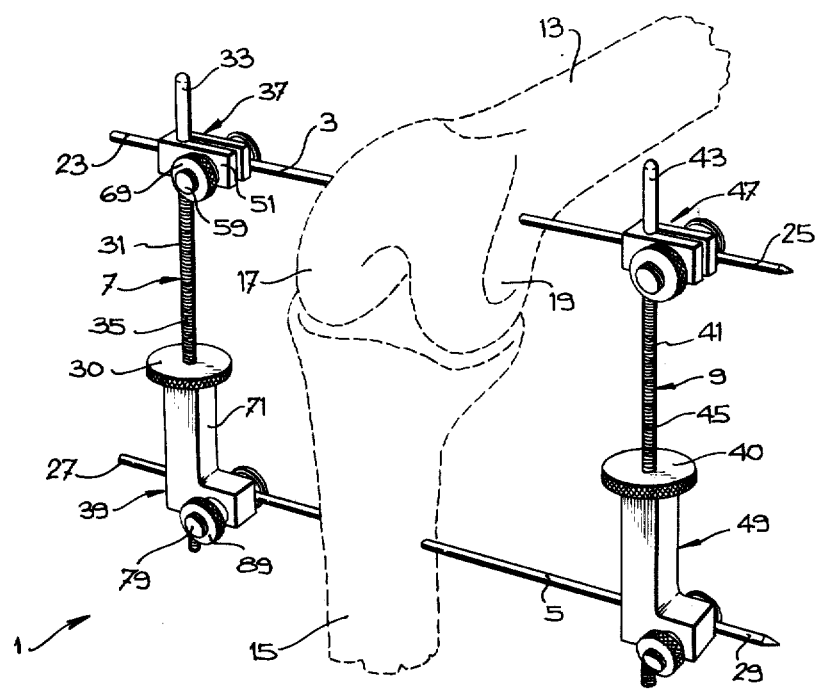
FIG. 1 represents a perspective view of an embodiment of the joint distractor according to the invention used in knee arthroplasty.

The biplanar joint distractor 1 shown in FIG. 1 in operative position for use in human knee arthroplasty, comprises a pair of upper and lower pins 3 and 5 removably introduced transversally through the patient's femur 13 and tibia 15 respectively, and a pair of mechanically adjustable means 7 and 9 fixed onto the ends of the pins 3 and 5 at a predetermined distance on both sides of the femur 13 and tibia 15.

As is shown in FIG. 1, the upper pin 3 which may be for example, a conventional 3/16 inch Steinmann pin, is introduced laterally through the patient's femoral condyles 17 and 19 in a direction perpendicular to the long axis of the femur 13, after having exposed the patient's knee joint by medial parapatellar incision of the skin of the knee, removal of the fat pad, release of the anterior medial capsule and lateral dislocation of the patella, according to a known surgical procedure. Because of its specific orientation and positioning, the upper pin 3 advantageously keeps retracted the exterior mechanism (not shown) of the knee and may be used for immobilizing the laterally dislocated patella (also not shown).

The lower pin 5 which may also be, for example, a conventional 3/16 inch Steinmann pin, is introduced in the patient's tibia 15 laterally through the soft tissue of the bone in a direction substantially parallel to that of the upper pin 3 about five inches below the latter.

The upper and lower pins 3 and 5 are connected to each other on both sides of the femur 13 and tibia 15 by the mechanically adjustable means 7 and 9 which are identical to each other and extend from the left and right ends 23 and 25 of the upper pin 3 to the left and right ends 27 and 29 of the lower pin 5, respectively.

The adjustable means 7 comprises a partially threaded rod 31 with a short, not threaded upper portion 33 and a long, continuously threaded lower portion 35. The adjustable means 7 also comprises first means 37 for rigidly fixing the upper portion 33 of the rod 31 to the end 23 of the upper pin 3 and second means 39 which is rigidly fixed to the end 27 of the lower pin 5 but slidably mounted on the lower portion 35 of the rod 31. These first and second means 37 and 39 will be described hereinafter in more details with reference to FIGS. 2 and 3 of the drawings. In addition, the adjustable means 7 comprises a serrated wheel 30 threadably mounted on the lower threaded portion 35 of the rod 31 between the first means 37 and the second means 39.

Similarly, the adjustable means 9 comprises a partially threaded rod 41 with a short, not threaded upper portion 43 and a long, continuously threaded lower portion 45; first means 47 for rigidly fixing the upper portion 43 of the rod 33 to the other end 25 of the upper pin 3; second means 49 which is rigidly fixed to the other end 29 of the lower pin 5 but slidably mounted on the lower portion 45 of the rod 33; and a serrated wheel 40 threadably mounted on the lower portion 45 of the rod 41 between the first means 47 and the second means 49. Each of these elements are structurally identical to those of the adjustable means 9 and therefore will not be further detailed.

Figure 2:
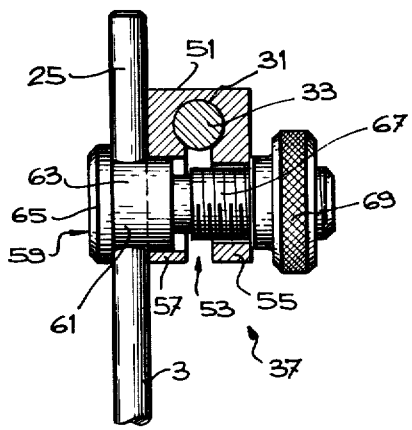
FIG. 2 represents a bottom plan view of the first means for rigidly fixing the mechanically adjustable means to one of the pins, in partial cross-section.

Referring now to FIG. 2 of the drawings, the first means 37 which is used for rigidly fixing the upper, not threaded portion 33 of the rod 31 to the end 23 of the upper pin 3, comprises a U-shaped member 51 with two parallel arms 55 and 57 defining a slot 53. The first means 37 also comprises a partially threaded pin 59 passing and extending outwards the surfaces of both of the arms 55 and 57 in a direction perpendicular to the axis of the slot 53 and a serrated wheel 69 threaded on the pin 59. The slot 53 of the U-shaped member 51 has a rounded bottom especially designed to receive and hold the upper portion 33 of the rod 3 passing therethrough perpendicularly to the axes of the slot 53 and pin 25, respectively. The fixing pin 59 passing transversally through the U-shaped member 51, is of a round cross-section and comprises a first external and not threaded portion 61 with a transversal hole 63 in which is inserted the end 25 of the upper pin 3, and a second external threaded portion 67 which coaxially extends the first section 61. The first section 61 which passes through a corresponding hole in the arm 57 of the U-shaped member 51, is ended by an integral, coaxial disc 65 having a diameter higher than that of the first section, which disc 65 is adjacent to the periphery of the transversal hole 63. The second section 67 which passes through another corresponding hole in the arm 55 of the U-shaped member 51, is of a smaller diameter than that of the first section 61 and receives the serrated wheel 69 which is threaded onto its free outer end.

As can be understood, screwing down of the wheel 69 onto the fixing pin 59 allows for simultaneous clamping of the end 25 of the pin 3 passing through the hole 63 adjacent the outer surface of the arm 57 of the U-shaped member 51 by contact against the same, and of the end 33 of the rod 31 between the arms 55 and 57 of the U-shaped member 51 by contraction of the same.

Owing to the particular arrangement of the U-shaped member 51 and fixing pin 59 which may rotate about its axis perpendicularly to the axis of the slot 53, the upper pin 3 and rod 31 do not have to be exactly perpendicular to be fixed to each other. Actually, the angle between the upper pin 3 and rod 31 may be varied about the axis of the fixing pin 59 thus advantageously allowing for safe and reliable fixation of the upper and lower pins 3 and 5 introduced in the patient's femur and tibia even when the latter are not exactly parallel to each other.

Figure 3:
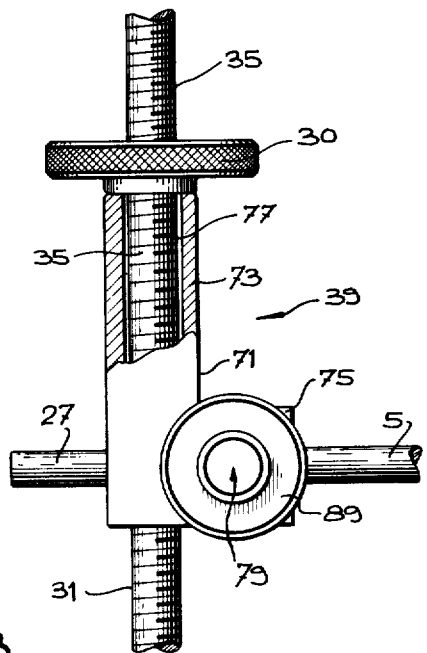
FIG. 3 represents a front elevational view of the second means slidably mounted on each of the rods, in partial cross-section.

Referring now to FIG. 3 of the drawings, the second means 39 which is rigidly fixed to the end 27 of the lower pin 5 but slidably mounted on the lower portion 35 of the rod 31, comprises a L-shaped member 71 with a vertical, longer arm 73 and an horizontal shorter arm 75. The longer arm 73 is pierced by a cylindrical hole 77 extending along its longitudinal axis while the shorter arm 75 is pierced by another cylindrical hole (not shown) extending transversally in a direction perpendicular to the longitudinal axis of the longer arm 73. The cylindrical hole 77 of the longer arm 73 is of such a diameter as to receive the lower threaded portion 35 of the rod 31 in a slidable manner and to guide the same. The cylindrical hole (not shown) of the shorter arms 75 is of such a shape as to receive a fixing pin 79 substantially identical to the fixing pin 59, with a first, not threaded portion pierced by a hole in which is inserted the end 27 of the lower pin 5 a second threaded portion extending the first one and a serrated wheel 89 threaded onto the free end of the second portion.

As above described with reference to the first means 37, screwing down of the wheel 89 onto the fixing pin 79 allows for rigid fixation of the end 27 of the lower pin 5 passing through the hole of the not threaded portion of the fixing pin 79 by contact against the outer surface of the shorter arm 79 of the L-shaped member 71.

Owing to the particular arrangement of the L-shaped member 71 and fixing pin 79, the lower pin 5 and rod 31 do not have to be exactly perpendicular to be fixed to each other. Actually the angle between the lower pin 5 and rod 31 may be varied about the axis of the fixing pin 79, thus advantageously allowing for safe and reliable fixation of the lower pin 5 introduced in the patient's tibia 15 even when the lower pin is not exactly parallel to the upper one.

As aforesaid, the serrated wheels 30 and 40 are, in use, threadably mounted on the lower threaded portion 35 and 45 of rods 31 and 41 respectively, between the first and second means.

The above described joint distractor 1 is operated as follows.

After introduction of the upper and lower pins 3 and 5 in their respective position in the patient's femur 13 and tibia 15 respectively and optional appliance of a preliminary manual traction onto the pins to stretch the ligaments, the serrated wheels 30 and 40 are screwed on the rods 31 and 41 respectively and the latter are fixed by their first and second means 37, 47, 39 and 49 to the ends of pins 3 and 5, respectively. The wheels 30 and 40 which are located between the first and second means, are then rotated downwardly so as to contact the upper ends of the upper arms of the second means 39 and 49 respectively and to force the latter to slide down along the rods 31 and 41 apart of the first means 37 and 47 respectively, thus applying further traction onto the pins 3 and 5 until the latter are sufficiently separated and/or the ligaments are adequately taut.

During this operation, the tension in the ligaments is checked by palpation.

Once the operation, such as a total knee arthroplasty, is completed, the wheels 30 and 40 are rotated upwardly so as to let the second means freely slide back along the rods 31 and 41 towards the first means under the action of the ligaments which are naturally reestablishing their lengths.

The joint distractor 1 has a number of advantages.

First of all, it allows the surgeon to preserve the collateral and cruciate ligaments of the knee during the operation and to reestablish at will the lengths of the same such as, for example, immediately after joint exposure in total knee arthroplasty, for the purpose of determining the amount of bone resection required to maintain knee stability.

It also allows the surgeon to obtain more working space in the knee and to immobilize the latter throughout the procedure. This particularly helps in preventing any accidental movement which may rupture the anterior cruciate ligament in surgery.

Moreover, owing to their original structures, the first and second means used for fixing the rods 31 and 41 to the pins 3 and 5 allow for distraction of the knee in either full extension and/or at 90 degrees flexion without dimantling the whole distractor 1, while the operating wheels 30 and 40 allow for individual distraction and correction of the collateral ligaments, thus providing the surgeon with an opportunity to consider whether or not soft tissue are necessary.

Finally, the joint distractor 1 allows for restoration of the correct axial alignment of the limbs because the collateral ligaments become taut as the knee is distracted and in most instances where there is no fixed lateral deformity, the length of the ligaments are not altered.

While the above description has been made only with reference to knee arthroplasty, it will be understood that the joint distractor 1 can be used with similar efficiency and advantages in other joint arthroplasty, such as, for example, elbow arthroplasty.

I claim:

1. A biplanar joint distractor to be used in arthroplasty for reversibly separating two articulated bones joined by at least one ligament while preserving the latter, said joint distractor comprising a pair of pins each to be removably introduced transversaly through one of the bones to be separated and a pair of mechanically adjustable means fixable onto said pins at a predetermined distance on both sides of the bones for forcing said bones apart, said adjustable means comprising:

a pair of at least partially threaded rods extending generally perpendicular to said pins, first means for rigidly fixing each rod by one of its ends to one end of one of said pins, said first means comprising a U-shaped member with two parallel arms defining a slot in which is inserted the upper end of one of the rods, a first, partially threaded fixing pin passing through and extending outwards the surfaces of both of the arms in a direction perpendicular to the axis of the slot, said first fixing pin comprising a first, external, not threaded portion with a transversal hole in which is inserted the end of one of the pin and a second, external, threaded portion, and a first serrated wheel threaded onto the second portion of said first fixing pin, whereby rotation of said first serrated wheel downwards onto said first fixing pin allows for simultaneous clamping of said one pin by contact against the surface of one of said arms and of said one rod by contraction of said arms, second means slidably mounted on each of said rods, including means thereon for clamping the ends of the other pin; and a pair of operating wheels each threadably mounted on the threaded portion of one of said rods between said first and second means, whereby rotation of said operating wheels in one direction brings said operating wheels in contact against said second means and forces the latter to slide along the rods apart from the first means while rotation of said wheels in the other direction lets said second means freely slide back along the rods towards the first means.

2. A biplanar joint distractor as claimed in claim 1, wherein the second means comprises a L-shaped having a vertical, longer arm with a cylindrical hole extending along its longitudinal axis in which is slidably inserted the lower end of one of the rods, and a horizontal shorter arm with another cylindrical hole perpendicular to the first one and in which is inserted a second fixing pin having a first, external, not threaded portion with a transversal hole in which is inserted the end of the other pin and a second external, threaded portion, and a second serrated wheel threaded onto the second portion of said second fixing pin, whereby rotation of said second serrated wheel downwards onto said second fixing pin allows for clamping of said other pin by contact against the surface of said horizontal, shorter arm.

* * * * *